United States Patent [19]

Kelsey

[11] Patent Number: 5,527,973
[45] Date of Patent: Jun. 18, 1996

[54] PURIFICATION OF 1,3-PROPANEDIOL

[76] Inventor: Donald R. Kelsey, 4706 Lake Village Dr., Fulshear, Tex. 77441

[21] Appl. No.: 357,832

[22] Filed: Dec. 16, 1994

[51] Int. Cl.$^6$ .................................................. C07C 29/141
[52] U.S. Cl. ........................................................... 568/862
[58] Field of Search .................................... 568/810, 852, 568/854, 856, 700, 862

[56] References Cited

U.S. PATENT DOCUMENTS

| | | | |
|---|---|---|---|
| 4,105,701 | 8/1978 | Larkin | 260/650 |
| 5,334,778 | 8/1994 | Haas et al. | 568/862 |

Primary Examiner—José G. Dees

[57] ABSTRACT

A process is described for purifying a carbonyl-containing 1,3-propanediol composition, the process comprising:

(a) forming a solution of said 1,3-propanediol composition in an acidic aqueous medium;

(b) adding a sufficient amount of a base to the aqueous medium to form a basic solution having a pH greater than 7;

(c) heating the basic solution under conditions effective to distill a major portion of the water therefrom; and (d) heating the remaining basic solution under conditions effective to distill a major portion of the PDO therefrom, to provide a 1,3-propanediol composition having a lower carbonyl content than the starting carbonyl-containing 1,3-propanediol composition.

The process of the invention provides a purified 1,3-propanediol which can be used as a starting material for a low-color polyester.

18 Claims, No Drawings

PURIFICATION OF 1,3-PROPANEDIOL

BACKGROUND OF THE INVENTION

This invention relates to the preparation of 1,3-propanediol. In a specific aspect, the invention relates to the recovery of 1,3-propanediol from a reaction product mixture containing carbonyl impurities.

1,3-Propanediol (PDO) is an important industrial chemical useful in the preparation of poly(propylene terephthalate) (PPT), a polyester from which films and fibers can be made. PDO can be prepared from ethylene oxide in a process involving cobalt-catalyzed hydroformylation followed by hydrogenation, and it can alternatively be prepared by hydrolysis of acrolein in the presence of an acid catalyst followed by hydrogenation. In the preparation of PDO, it is common for the crude product to include 400 ppm or more carbonyl by-products including acetals. High levels of carbonyl impurities in PDO are associated with the production of acrolein during preparation of PPT and with poor color in fibers spun from the PPT.

It is therefore an object of the invention to provide a process for purifying 1,3-propanediol. In one aspect, it is an object of the invention to provide a process which reduces the carbonyl content of PDO and reduces the amount of acrolein by-product in the condensation polymerization to PPT.

SUMMARY OF THE INVENTION

According to the invention, a process is provided for purifying a carbonyl-containing 1,3-propanediol composition, the process comprising:

(a) forming a solution of the 1,3-propanediol composition in an aqueous medium having a pH less than 7;

(b) adding a sufficient amount of a base to said acidic solution to form a basic solution having a pH greater than 7;

(c) heating the basic solution under conditions effective to distill a major portion of the water therefrom; and (d) heating the remaining basic solution under conditions effective to distill a major portion of the 1,3-propanediol therefrom, to provide a 1,3-propanediol composition having a lower carbonyl content than the starting carbonyl-containing 1,3-propanediol composition.

The process of the invention provides a purified PDO which can be used as a starting material for a low-color polyester.

DETAILED DESCRIPTION OF THE INVENTION

The invention process involves forming an acidic aqueous solution of a carbonyl-containing 1,3-propanediol composition. The source of the contaminating carbonyl species can be acetals, aldehydes or ketones. The amount of water in or added to the PDO will generally be that sufficient to provide an aqueous solution of about 5 to about 95 weight percent water, preferably about 10 to about 80, and most preferably about 20 to about 70 weight percent water. Less dilute PDO solutions have the advantage of requiring less subsequent purification and smaller equipment, with the disadvantage of requiring longer times for removal of impurities. More dilute solutions can be purified in less time but require larger equipment and may not be as efficient because of the need to remove large amounts of water. The water is preferably distilled or deionized water.

An acid is added to the aqueous PDO solution. The pKa (25° C.) of the acid in aqueous solution is less than about 6, preferably less than about 4. The acid may be organic or inorganic and preferably has a high (greater than about 100° C.) boiling point so as not to be easily removed if sparging or vacuum is applied to the solution. Examples of suitable acids include carboxylic acids, preferably $C_2$ or greater, such as succinic, propionic, hexanoic, chloroacetic or benzoic acid; sulfonic acids particularly arylsulfonic acids such as p-toluenesulfonic acid; hydrohalide acids; phosphoric acids including orthophosphoric acid and metaphosphoric acid; and compounds which can generate acids in the presence of water or hydroxyl groups, such as sulfur trioxide, phosphorus pentoxide, carboxylic anhydrides and Lewis acids such as aluminum chloride. Sulfonic and phosphoric acids are preferred. The acid may also be in insoluble form as, for example, an acidic polymeric ion exchange resin, acidic alumina or acidic clay, in which case it is desirable to remove the solid acid by filtration or other suitable means before distillation of the aqueous solution. Mixtures of suitable acids may be used. In general, oxidizing acids such as sulfuric acid and nitric acid can be used but may cause unwanted side reactions. Acids containing heavy metals or halogens would not be preferred because of possible adverse effects on PDO quality from contamination by metal or halide ions.

The amount of acid added to the aqueous solution is that which is sufficient to achieve a pH of less than 7, preferably less than about 5, most preferably less than about 4. Typical pH levels will fall within the range of about 2 to about 6, with low levels of acid generally requiring longer reaction times than higher levels of acid (lower pH). However, very large amounts of acid are unnecessary, will increase the cost of the reaction and may cause unwanted side reactions. In the case of insoluble acids, the pH of the solution may remain relatively high, i.e. close to 7. If the starting PDO composition is acidic, it is nonetheless generally advisable to form the aqueous solution with added acid.

In an optional but preferred embodiment of the invention process, the aqueous acidified PDO solution is sparged with a gas to aid in the removal of volatile impurities. The gas is preferably an inert gas such as nitrogen, argon or helium, with nitrogen preferred. The rate of sparging will affect the efficiency of removal of volatiles and is typically in the range of about 0.01 to about 10 liters/minute per liter of aqueous PDO solution. Instead of or in addition to sparging, reduced pressure can also be applied to facilitate the removal of volatile impurities. In the latter embodiment, preferred operating pressures will generally fall within the range of about 100 to about 900 mbar. In any embodiment, the acid treatment is preferably accompanied by stirring of the aqueous medium.

As the volatile impurities are removed from the PDO solution, they are recovered by suitable means, such as appropriate scrubbers or by passage into a caustic solution.

The temperature during the acid treatment can affect the rate of removal of the impurities and will generally fall within the range of about 0 to about 100° C. preferably within the range of about 5 to about 60° C. Temperatures above about 50° C., i.e., near or above the boiling point of acrolein, can promote removal of volatile impurities, such as acrolein, formed in this step. Although higher temperatures can be used, particularly for short periods, high temperatures can promote undesired side reactions, especially acid-catalyzed reactions.

The treatment time will vary depending upon the other reaction conditions such as level of impurities, the desired PDO purity, the amount of water and acid, the sparging (or vacuum) efficiency and the reaction temperature. Under preferred reactions conditions, the time of the acid treatment will usually be at least about 30 minutes, generally within the range of about 1 to about 24 hours, preferably less than about 6 hours.

Following the acid treatment, the aqueous solution is adjusted to a pH greater than 7, preferably to a pH of about 8 or more, by the addition of a base. The amount of base is nominally the amount needed to neutralize the acid present in the first step, although additional base may be desirable, particularly if the starting PDO composition contained acidic species. The preferred bases are the alkali and alkaline earth hydroxides, carbonates and bicarbonates, particularly sodium and potassium hydroxides. The addition of base may cause yellowing of the PDO. For PDO solutions acidified with an insoluble acid such as an acidic resin, the base is preferably added after the acid has been physically removed by filtration or other suitable means.

The basic aqueous solution is then distilled to remove water. The distillation can be carried out at atmospheric pressure but is most efficiently carried out under reduced pressure within the range of about 100 mbar to about 600 mbar. Typical distillation equipment such as distillation and fractionation columns can be used.

After the water and other low-boiling components are removed, the PDO can be distilled overhead, preferably at a temperature within the range of about 100 to about 160° C. and at reduced pressure (typically at less than about 200 mbar) to avoid excessive heating of the PDO. Distillation typically removes the yellow color generated in the neutralization step, i.e., the distillate is water-white whereas the residue may be highly colored.

Each of the process steps can be carried out independently as batch, semi-batch, semi-continuous or continuous processes.

The purified PDO can be used, for example, to prepare condensation polymers and copolymers. The purified PDO is particularly useful for preparing poly(propylene terephthalate) by the condensation polymerization of PDO with terephthalic acid.

EXAMPLE 1

In this and the following examples, carbonyl analyses were made using a test based on ASTM E411-70 in which total carbonyls (from both acetals and free carbonyl) were determined by conversion to 2,4-nitrophenylhydrazone derivatives and measured colorimetrically. The carbonyls are reported in ppm based on C=O.

A flask with a magnetic stir bar was charged with 250 g of 1,3-propanediol (carbonyl content 665 ppm) and 250 ml deionized water. The pH of the resulting solution was about 4.5–5. Phosphoric acid (0.23 g, 85 wt %) was added to the solution to adjust the pH to about 3–3.5. The solution was stirred at room temperature (about 23° C.) for about 5 hours. A sample of the solution had a carbonyl content of 217 ppm. The acidic aqueous solution was then neutralized and adjusted to a pH of about 10–10.5 by addition of 8.5 ml of 1N sodium hydroxide solution. The basic reaction solution was distilled using a 20-cm Vigreux column to remove the water and a small forecut of 1,3-propanediol (combined total 262 g), and the major portion of purified, water-white 1,3-propanediol was distilled over at about 124° C. (oil bath temperature 153–157° C.) and about 30 mbar. The purified 1,3-propanediol (203 g) had a carbonyl content of 245 ppm. The distillation residue (about 29 g) was tannish orange and had a carbonyl content of 685 ppm.

EXAMPLE 2

A flask with magnetic stir bar was charged with 750 ml commercial 1,3-propanediol (carbonyl content 365 ppm, average of two analyses), 750 ml purified water (EM Omnisolve HPLC grade) and, 0.6 g p-toluenesulfonic acid monohydrate. The solution was stirred at room temperature and sparged with a fine stream of nitrogen bubbles at about 0.4 liters per minute via a glass sparge tube with a sintered glass tip immersed to the bottom of the flask. After about 5 hours, 0.16 g phosphoric acid (85%) was added to the mixture. After a total of about 88 hours, the solution (carbonyl analysis 137 ppm) was made basic by addition of about 14 ml 1N solution of sodium hydroxide, which caused the reaction mixture to turn slightly yellow. The basic solution was transferred to a distillation flask and heated at an oil bath temperature of about 125–130° C. under a reduced pressure of about 400 mbar to remove the water. After about 4 hours, about 701 g aqueous distillate had been collected. Over a period of about 3 hours, the pressure was reduced gradually from about 400 mbar to about 110 mbar and held for a time at this pressure to collect an additional 28 g aqueous distillate. The oil bath temperature was then raised to about 150°–155° C. at 110 mbar, and the pressure was reduced until steady distillation of the PDO occurred at about 80-90 mbar. The first 100 ml of this distillate was discarded and the middle cut of purified, water-white PDO was collected. A yellow residue (about 80 g) was left in the distillation flask. The purified PDO showed no detectable acrolein by GC, and colorimetric analysis showed 128 ppm carbonyls.

EXAMPLE 3

A flask with magnetic stir bar was charged with 800 g commercial 1,3-propanediol (average carbonyl analysis 365 ppm), 200 g water and 0.5 g p-toluenesulfonic acid monohydrate. The stirred mixture was sparged as in Example 2 at room temperature for about 17 hours, heated gently with sparging on a hot plate to 41°–66° C. for about 3 hours, and cooled to room temperature. After a total of about 25 hours, about 7 ml 1N sodium hydroxide solution was added to bring the pH to between 7 and 8. The PDO solution turned slightly yellow. The reaction solution was distilled as in Example 2 at a bath temperature of about 140° C. at atmospheric pressure, then at about 150°–160° C., then at about 125° C. at about 400 mbar and decreasing to about 110 mbar, then at 150° C. at about 60–70 mbar. Analyses showed 216 ppm carbonyls in the PDO in the distillation flask after removal of most of the water and 178 ppm carbonyls in the final, distilled (455 g), water-white PDO.

EXAMPLE 4

A 100-ml 3-neck flask fitted with a magnetic stir bar and short path distillation head with chilled water cooling on the condenser was charged with 40 g PDO (color 5 or less by ASTM D-1209; acrolein less than 10 ppm by gas chromatography) and 0.008 g p-toluenesulfonic acid monohydrate. The mixture was thoroughly degassed at least five times using a Firestone valve with purified nitrogen or argon and then heated in a 225° C. oil bath for three hours and then cooled to room temperature. The collected aqueous distillate was weighed and analyzed by gas chromatography for acrolein and allyl alcohol using an internal standard. Table 1 shows the amount of acrolein and allyl alcohol collected based on the distillate weight and analysis. The color of the PDO after this reaction was measured according to ASTM method D-1209 (using 35-ml samples) and is shown in Table 1.

TABLE 1

|  | PDO Carbonyls[a] (ppm) | Acrolein (mg) | Allyl Alcohol (mg) | Color[c] |
| --- | --- | --- | --- | --- |
| Commercial[b] | 1100 | 11.6 | 27 | 250–300 |
| Commercial | 365 | 4.2 | 20 | 100 |
| Commercial | 365 | 3.1 | 22 | ND[d] |
| Example 2 | 128 | 2.9 | 26 | 5–10 |
| Commercial | 112 | 0.3 | 10 | 50 |

[a]Average, as C = O.
[b]Distilled only.
[c]Pt—Co scale.
[d]ND = not determined.

Note from Table 1 that the PDO purified in Example 2 produced less acrolein than the unpurified PDOs with higher carbonyl contents. The color of the PDO after heating with acid was the lowest with the purified PDO of Example 2, which was even lower in color than the untreated PDO having somewhat lower carbonyl content.

EXAMPLE 5

In this experiment, PDO was polymerized with terephthalic acid to produce a polyester. A 600-ml stainless steel pressure reactor fitted with a distillation column, condenser and collection vessel was charged with 133.2 g of the indicated (Table 2) 1,3-propanediol (1.75 mole; acrolein less than 10 ppm by gas chromatography) and 207.7 g terephthalic acid (1.25 mole). The reactor was pressurized to 50–80 psi with nitrogen, degassed by release of pressure five times, and repressurized to 20 psi and heated to 150° C. For the first two hours, the pressure was maintained near 50 psi and was lowered in 10 psi increments each hour thereafter. After a total of about 6 hours, any pressure was released and the aqueous distillate was collected, weighed and analyzed by GC. The molten oligomer was poured into a pan and cooled. The yellowness index of the oligomer was measured by reflectance with a Gardner Colorgard System 105 according to ASTM D-1925. Results are shown in Table 2.

TABLE 2

| PDO | Carbonyl[a] (ppm) | Aqueous Distillate | | | PPT Color (Yellowness Index) |
| --- | --- | --- | --- | --- | --- |
|  |  | Distillate (g) | Acrolein (ppm) | Allyl Alcohol (%) |  |
| Commercial[b] | 1100 | 47.3 | 4390 | 1.2 | 13 |
| Commercial | 365 | 45.2 | 2120 | 0.8 | 6.6 |
| Example 3 | 178 | 48.9 | 1320 | 0.7 | −0.5 |
| Example 2 | 128 | 45.9 | 1460 | 0.8 | −0.6 |
| Commercial | 112 | 44.7 | 1170 | 0.8 | 4.7 |

[a]Average, as C = 0.
[b]Distilled only.

As can be seen from Table 2, the purified PDOs from Examples 2 and 3 gave less acrolein by-product in the aqueous distillate than the PDOs having higher total carbonyl analyses. The purified PDOs also gave an oligomeric PPT product with low yellowness index.

EXAMPLE 6

A larger-scale preparation of PDO by the invention process was carried out as follows:

A 100-gallon reactor was charged with 394.3 lbs. of 1,3-propanediol containing about 212 ppm (average) carbonyl impurities and 275 lbs. deionized water. A mixture of 38.6 g 85 wt % phosphoric acid and 143.7 g p-toluenesulfonic acid monohydrate was added to the reactor. The pH of the reactor mixture dropped to 2.6 following addition of the acid. Sodium hydroxide solution (1N, 131.5 ml) was added at ambient temperature and pressure to adjust the pH to about 3.1. Nitrogen sparging was carried out by introducing nitrogen gas at 80 psig via a dip tube extending to the bottom portion of the reactor. Nitrogen flow rate was 72 to 100 scfh. The surface of the liquid was covered with an even spread of nitrogen bubbles. The solution was vigorously agitated with a stirrer.

Two hours into the nitrogen sparge, the reactor was heated briefly from 32° C. to 70° C. and then allowed to cool to 45° C., where it remained during the remainder of the nitrogen sparge.

After six hours, a sample of the solution showed about 60 ppm carbonyls. Sparging was continued for a total of about 51 hours. After the nitrogen flow was stopped, the pH of the solution was adjusted to 8.2 by addition of 1810 ml of 1N sodium hydroxide solution. Vacuum was applied to distill off the water. The initial boiling point of the mixture was 85° C. at 305 mm Hg. The pH of the water distillate averaged 4.5. After removal of 191.9 lbs. of water, the PDO solution pH was about 7.8. The amount of PDO in the water cut was about 6.6 lbs.

The PDO/water fraction was distilled by decreasing the pressure to about 85 mm Hg. The boiling temperature was about 153° C. Thirty-four lbs. of PDO/water was removed. The pressure was then decreased to about 65 mm Hg to distill the PDO. The distillate from the first half hour (64 lbs.) was considered the PDO forecut. The concentration of this forecut was about 98 wt % PDO. The boiling point at 65 mm Hg was about 146° C. After 3 hours, the pressure was decreased further to 55mmHg to distill the remaining PDO. Total PDO middle cut collected was 283 lbs., which was shown to have about 48 ppm carbonyls (average). About 6.5 lbs. of highly-colored bottoms liquid remained in the reactor.

I claim:

1. A process for purifying a carbonyl-containing 1,3-propanediol composition, the process comprising:

(a) forming a solution of said 1,3-propanediol composition in an aqueous medium having a pH less than 7;

(b) adding a sufficient amount of a base to the aqueous medium to form a basic solution having a pH greater than 7;

(c) heating the basic solution under conditions effective to distill a major portion of the water therefrom; and (d) heating the remaining basic solution under conditions effective to distill a major portion of the 1,3-propanediol therefrom, to provide a distilled 1,3-propanediol composition having a lower carbonyl content than the starting carbonyl-containing 1,3-propanediol composition.

2. The process of claim 1 in which step (a) comprises adding an acid selected from the group consisting of $C_2$ or greater carboxylic acids, sulfonic acids, hydrohalide acids, phosphoric acids, Lewis acids, acidic polymeric ion exchange resins, acidic aluminas and acidic clays to an aqueous solution of said 1,3-propanediol composition.

3. The process of claim 1 in which the solution of step (a) comprises at least one of p-toluenesulfonic acid and phosphoric acid.

4. The process of claim 1 in which the solution of step (a) has a pH less than about 4.

5. The process of claim 1 in which step (a) is carried out under a gas sparge with a gas selected from the group consisting of nitrogen, argon and helium.

6. The process of claim 1 in which step (a) is carried out over a time within the range of about 1 to about 6 hours.

7. The process of claim 6 in which the solution of step (a) is maintained at a temperature within the range of about 5° to about 60° C.

8. The process of claim 1 in which the solution of step (a) comprises about 20 to about 70 weight percent water.

9. The process of claim 1 in which the base added in step (b) is selected from sodium hydroxide and potassium hydroxide.

10. The process of claim 1 in which step (a) is carried out under a pressure less than about 900 psig.

11. A process for purifying a carbonyl-containing 1,3-propanediol composition, the process comprising:
(a) forming a solution of said 1,3-propanediol composition in an aqueous medium having a pH less than 5 and maintaining the resulting solution under a gas sparge for a time within the range of about 1 to about 6 hours;
(b) adding a sufficient amount of a base to the aqueous medium to form a basic solution having a pH greater than about 8;
(c) heating the basic solution under conditions effective to distill a major portion of water therefrom;
(d) heating the remaining basic solution under conditions effective to distill a major portion of 1,3-propanediol therefrom, to provide a 1,3-propanediol composition having a lower carbonyl content than the starting carbonyl-containing 1,3-propanediol composition.

12. The process of claim 11 in which step (a) comprises adding an acid selected from the group consisting of $C_2$ or greater carboxylic acids, sulfonic acids, hydrohalide acids, phosphoric acids, Lewis acids, acidic polymeric ion exchange resins, acidic aluminas and acidic clays to an aqueous solution of said 1,3-propanediol composition.

13. The process of claim 11 in which the solution of step (a) comprises at least one of p-toluenesulfonic acid and phosphoric acid.

14. The process of claim 13 in which the solution of step (a) has a pH less than about 4.

15. The process of claim 11 in which step (a) is carried out at a pressure less than about 900 psig.

16. The process of claim 11 in which the solution of step (a) is maintained at a temperature within the range of about 5° to about 60° C.

17. The process of claim 11 in which the base added in step (b) is selected from sodium hydroxide and potassium hydroxide.

18. The process of claim 11 in which the solution of step (a) comprises about 20 to about 70 weight percent water.

* * * * *